US011203597B2

(12) United States Patent
Patterson et al.

(10) Patent No.: US 11,203,597 B2
(45) Date of Patent: Dec. 21, 2021

(54) CRYSTALLINE SPIROCYCLIC COMPOUND, A DOSAGE FORM CONTAINING, A METHOD FOR USING IN TREATMENT OF DISEASE, AND A METHOD FOR RECRYSTALLIZING

(71) Applicant: Altavant Sciences GmbH, Basel (CH)

(72) Inventors: Daniel Patterson, Durham, NC (US); Shanie Everts, Maasbracht (NL)

(73) Assignee: Altavant Sciences GmbH, Basel (CH)

( * ) Notice: Subject to any disclaimer, the term of this patent is extended or adjusted under 35 U.S.C. 154(b) by 0 days.

(21) Appl. No.: 16/683,509

(22) Filed: Nov. 14, 2019

(65) Prior Publication Data

US 2020/0148681 A1 May 14, 2020

Related U.S. Application Data

(60) Provisional application No. 62/767,171, filed on Nov. 14, 2018.

(51) Int. Cl.
  *C07D 471/10* (2006.01)
  *A61K 9/00* (2006.01)
(52) U.S. Cl.
  CPC ............ *C07D 471/10* (2013.01); *A61K 9/007* (2013.01); *C07B 2200/13* (2013.01)
(58) Field of Classification Search
  CPC .................................................. C07D 471/10
  See application file for complete search history.

(56) References Cited

U.S. PATENT DOCUMENTS 9,199,994 B2 * 12/2015 De Lombaert ...... C07D 471/10

FOREIGN PATENT DOCUMENTS

WO 2015035113 A1 3/2015

OTHER PUBLICATIONS

Matthes et al. Trends in Pharmacological Sciences, Jun. 2018, vol. 39, No. 6, p. 560-572 (Year: 2018).*
Aiello et al. J.Pharmacol Exp. Ther. vol. 360 p. 267-279 . (Year: 2017).*
Mawe et al., "Serotonin signaling in the gut—functions, dysfunctions and therapeutic targets," Nature-Gastroenterology & Hepatology, Aug. 2013, 10:473-486.
Gershon, M. D. "5-hydroxytryptamine (serotonin) In The Gastrointestinal Tract". Current Opinion in Endocrinology, Diabetes, and Obesity 20, 14-21 (2013).
Lesurtel et al., "Role of Serotonin In The Hepato-gastrointestinal Tract: An Old Molecule For New Perspectives," Cell. Mol. Life Sci., 2008 65:940-952.
Kode et al., "FOXO1 orchestrates the bone-suppressing function of gut-derived serotonin," J. Clinical Investigation, Jul. 2012.
Yadav et al., "Pharamacological inhibition of gut-derived serotonin synthesis is a potential bone anabolic treatment for osteoporosis," Nature Medicine, Feb. 2010, 1-14.
Yadav et al., "Lrp5 Controls Bone Formation by Inhibiting Serotonin Synthesis in the Duodenum," Cell, Nov. 2008, 135:825-837.
Liang et al., "Serotonin Promotes The Proliferation Of Serum-deprived Hepatocellular Carcinoma Cells Via Upregulation Of FOXO3a," Molecular Cancer, 2013, 12:14.
Soll et al., "Serotonin Promotes Tumor Growth in Human Hepatocellular Cancer," Hepatology 2010, 51(4):1244-1254.
Pai et al., "Altered serotonin physiology in human breast cancers favors paradoxical growth and cell survival," Breast Cancer Research, Nov. 2009, 11(6):1-17.
Engelman et al., "Inhibition Of Serotonin Synthesis By Para-chlorophenylalanine In Patients With The Carcinoid Syndrome," The New England Journal of Medicine, Nov. 1967, 277:1103-1108.
Sumara et al., "Gut-derived Serotonin is a Multifunctional Determinant to Fasting Adaptation," Cell Metabolism, Nov. 2012, 16:1-13.
Ban et al., "Impact Of Increased Plasma Serotonin Levels and Carotid Atherosclerosis On Vascular Dementia," Atherosclerosis, 2007, 195, 153-159.
Manocha et al.,"Serotonin and GI Disorders: An Update on Clinical and Experimental Studies," Clinical and Translational Gastroenterology, 2012, 3:e13, 6 pages.
Ghia et al., "Serotonin has a key role in pathogenesis of experimental colitis," Gastroenterology, 2009, 137(5): 1649-1660.
Sikander et al., "Role of serotonin in gastrointestinal motility and irritable bowel syndrome," Clinica Chimica Acta, 2009, 403:47-55.
Galligan et al. "Recent advances in understanding the role of serotonin in gastrointestinal motility and functional bowel disorders," Neurogastroenterol Motil., 2007, 19(Suppl 2):1-4.
Costedio et al., "Serotonin And Its Role In Colonic Function And In Gastrointestinal Disorders," Diseases of the Colon and Rectum, Mar. 2007, 50(3): 376-88.
Gershon and Tack, "The Serotonin Signaling System: From Basic Understanding To Drug Development For Functional GI Disorders," Gastroenterology, 2007, 132:397-414.
Mawe et al., "Review article: intestinal serotonin signaling in irritable bowel syndrome," Aliment Pharmacol Ther, 2006, 23:1067-1076.
Crowell, "Role Of Serotonin In The Pathophysiology Of The Irritable Bowel Syndrome," British Journal of Pharmacology, 2004, 141:1285-93.
Lau et al., "The Role Of Circulating Serotonin In The Development Of Chronic Obstructive Pulmonary Disease," PloS One, Feb. 2012, 7(2):e31617, 7 pages.

(Continued)

*Primary Examiner* — Emily A Bernhardt
(74) *Attorney, Agent, or Firm* — Ohlandt, Greeley, Ruggiero & Perle, LLP

(57) ABSTRACT

There is a crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate that exhibits an XRPD pattern having a characteristic peak at 19.05±0.20 (° 2θ). There is also a pharmaceutical composition containing the compound. There is also a dosage form containing the crystalline compound and one or more pharmaceutically acceptable excipients. There is also a method for crystallizing/recrystallizing the compound. There is also a method for treating or preventing a disease with the compound.

12 Claims, 2 Drawing Sheets

(56) References Cited

OTHER PUBLICATIONS

Egermayer et al., "Role Of Serotonin In The Pathogenesis Of Acute And Chronic Pulmonary Hypertension," Thorax, 1999, 54:161-168.
Duerschmied et al., "Platelet Serotonin Promotes The Recruitment Of Neutrophils To Sites Of Acute Inflammation In Mice," Blood, Feb. 2013, 121(6):1008-1015.
Li et al., "Serotonin Activates Dendritic Cell Function In The Context Of Gut Inflammation," The American Journal of Pathology, Feb. 2011, 178(2):662-671.
Ebrahimkhani et al., "Stimulating Healthy Tissue Regeneration By Targeting The 5-HT2B Receptor in Chronic Liver Disease," Nature Medicine, 2011 17, 1668-1673.
Wacker et al., "Structural Features for Functional Selectivity at Serotonin Receptors," Science, May 2013, 340(6132):615-619.
Stokes et al., "p-Ethynylphenylalanine: A Potent Inhibitor of Tryptophan Hydroxylase," J Neurochemistry, 2000, 74(5):2067-2073.
Zhong et al., "Molecular Dynamics Simulation of Tryptophan Hydroxylase-1: Binding Modes and Free Energy Analysis to Phenylalanine Derivative Inhibitors," Int. J Molecular Sci, May 2013, 14:9947-9962.
Camilleri, "LX-1031, A Tryptophan 5-hydroxylase Inhibitor, And Its Potential In Chronic Diarrhea Associated With Increased Serotonin," Neurogastroenterol Motil., Mar. 2011, 23(3):193-200.
Cianchetta et al., "Mechanism of Inhibition of Novel Tryptophan Hydroxylase Inhibitors Revealed by Co-crystal Structures and Kinetic Analysis," Current Chemical Genomics, 2010, 4:19-26.
Jin et al., "Substituted 3-(4-(1,3,5-triazin-2-yl)-phenyl)-2-aminopropanoic Acids As Novel Tryptophan Hydroxylase Inhibitors," Bioorganic & Medicinal Chemistry Letters, 2009, 19:5229-5232.
Shi et al., "Modulation of Peripheral Serotonin Levels by Novel Tryptophan Hydroxylase Inhibitors for the Potential Treatment of Functional Gastrointestinal Disorders," J Med Chem, 2008, 51:3684-3687.
Liu et al., "Discovery And Characterization of Novel Tryptophan Hydroxylase Inhibitors That Selectively Inhibit Serotonin Synthesis In The Gastrointestinal Tract," J. Pharmacol. Exp. Ther, 2008, 325(1):47-55.
Margolis et al., "Pharmacological Reduction of Mucosal but Not Neuronal Serotonin Opposes Inflammation In Mouse Intestine," Gut, Jun. 2013, 1-10 (with Supplemental Information).
Ouyang et al., "Combined Structure-Based Pharmacophore and 3D-QSAR Studies on Phenylalanine Series Compounds as TPII1 Inhibitors," Int J Molecular Sci, 2012, 13:5348-5363.
Robiolio et al., "Carcinoid Heart Disease: Correlation of High Serotonin Levels with Valvular Abnormalities Detected by Cardiac Catheterization and Echocardiography," Circulation, 1995, 92:790-795.
Goldberg Daniel R et al:"Optimization of spirocyclic proline tryptophan hydroxylase-1 inhibitors", Bioorganic & Medicinal Chemistry Letters, vol. 27, No. 3, 2016 pp. 413-419, Elsevier Ltd.
Written Opinion and International Search Report for corresponding International application PCT/IB2019/001233, 10 pages, dated Mar. 26, 2020.
International Preliminary Report on Patentability for corresponding International application PCT/IB2019/001233, 7 pages, dated May 18, 2021.

* cited by examiner

CRYSTALLINE SPIROCYCLIC COMPOUND, A DOSAGE FORM CONTAINING, A METHOD FOR USING IN TREATMENT OF DISEASE, AND A METHOD FOR RECRYSTALLIZING

CROSS-REFERENCE TO A RELATED APPLICATION

This application claims priority from U.S. Provisional Application No. 62/767,171, filed Nov. 14, 2018, which is incorporated herein in its entirety.

BACKGROUND OF THE DISCLOSURE

Field of the Disclosure

The present disclosure relates to a crystalline spirocyclic compound that is useful in the treatment of disease or disorders associated with peripheral serotonin. More particularly, the present disclosure relates to a crystalline spirocyclic compound that is an inhibitor of tryptophan hydroxylase (TPH), that is useful in the treatment of disease or disorders associated with peripheral serotonin. Yet more particularly, there is a dosage form containing the crystalline spirocyclic compound. Still yet more particularly, there is a method for recrystallizing the crystalline spirocyclic compound.

Description of the Prior Art

Serotonin (5-hydroxytryptamine, 5-HT) is a neurotransmitter that modulates central and peripheral functions by acting on neurons, smooth muscle, and other cell types. 5-HT is involved in the control and modulation of multiple physiological and psychological processes. In the central nervous system (CNS), 5-HT regulates mood, appetite, and other behavioral functions. In the GI system, 5-HT plays a general prokinetic role and is an important mediator of sensation (e.g., nausea and satiety) between the GI tract and the brain. Dysregulation of the peripheral 5-HT signaling system has been reported to be involved in the etiology of several conditions (see for example: Mawe, G. M. & Hoffman, J., Serotonin Signalling in the Gut-functions, Dysfunctions and Therapeutic Targets. *Nature Reviews. Gastroenterology & Hepatology* 10, 473-486 (2013); Gershon, M. D. 5-hydroxytryptamine (serotonin) in the Gastrointestinal Tract. *Current Opinion in Endocrinology, Diabetes, and Obesity* 20, 14-21 (2013); Lesurtel, M., Soil, C, Graf, R. & Ciavien, P.-A. Role of Serotonin in the Hepato-gastrointestinal Tract: An Old Molecule for New Perspectives. *Cellular and Molecular Life Sciences: CMLS* 65, 940-52 (2008)). These include osteoporosis (e.g. Kode, A, et al., FOXO1 Orchestrates the Bone-suppressing Function of Gut-derived Serotonin, *The Journal of Clinical Investigation* 122, 3490-503 (2012); Yadav, V, K. et al., Pharmacological Inhibition of Gut-derived Serotonin Synthesis is a Potential Bone Anabolic Treatment for Osteoporosis. *Nature Medicine* 16, 308-12 (2010); Yadav, V. K, et al., Lrp5 Controls Bone Formation by Inhibiting Serotonin Synthesis in the Duodenum, Cell 135, 825-37 (2008)), cancer (e.g. Liang, C, et al., Serotonin Promotes the Proliferation of Serum-deprived Hepatocellular Carcinoma Cells Via Upregulation of FOX03a. *Molecular Cancer* 12, 14 (2013); Soil, C. et al., Serotonin Promotes Tumor Growth in Human Hepatocellular Cancer. *Hepatology* 51, 1244-1254 (2010); Pai, V. P et al., Altered Serotonin Physiology in Human Breast Cancers Favors Paradoxical Growth and Cell Survival. *Breast Cancer Research: BCR* 11, R81 (2009); Engelman, K., Lovenberg, W. & Sjoerdsma, A. Inhibition of Serotonin Synthesis by Para-chlorophenylalanine in Patients with The Carcinoid Syndrome. *The New England Journal of Medicine* 277, 1103-8 (1967)), cardiovascular (e.g. Robiolio, P. A, et al., Carcinoid Heart Disease: Correlation of High Serotonin Levels with Valvular Abnormalities Detected by Cardiac Catheterization and Echocardiography. *Circulation* 92, 790-795 (1995)), diabetes (e.g. Sumara, G., Sumara, O., Kim, J. K. & Karsenty, G. Gut-derived Serotonin is a Multifunctional Determinant to Fasting Adaptation. *Cell Metabolism* 16, 588-600 (2012)), atherosclerosis (e.g. Ban, Y. et al., Impact of Increased Plasma Serotonin Levels and Carotid Atherosclerosis on Vascular Dementia. *Atherosclerosis* 195, 153-9 (2007)), as well as gastrointestinal (e.g. Manocha, M. & Khan, W. I. Serotonin and GI Disorders: An Update on Clinical and Experimental Studies. *Clinical and Translational Gastroenterology* 3, el 3 (2012); Ghia, J.-E. et al., Serotonin has a Key Role in Pathogenesis of Experimental Colitis. *Gastroenterology* 137, 1649-60 (2009); Sikander, A., Rana, S. V. & Prasad, K. K., Role of Serotonin in Gastrointestinal Motility and Irritable Bowel Syndrome. *Clinica Chimica Acta; International Journal of Clinical Chemistry* 403, 47-55 (2009); Spiller, R, Recent Advances in Understanding the Role of Serotonin in Gastrointestinal Motility in Functional Bowel Disorders: Alterations In 5-HT Signalling and Metabolism in Human Disease. *Neurogastroenterology and Motility: The Official Journal of The European Gastrointestinal Motility Society* 19 Suppl 2, 25-31 (2007); Costedio, M. M., Hyman, N. & Mawe, G, M, Serotonin and its Role in Colonic Function and In Gastrointestinal Disorders. *Diseases of the Colon and Rectum* 50, 376-88 (2007); Gershon, M. D. & Tack, J., The Serotonin Signalling System: From Basic Understanding to Drug Development for Functional GI Disorders. *Gastroenterology* 132, 397-14 (2007); Mawe, G. M., Coates, M. D. & Moses, P. L. Review Article: Intestinal Serotonin Signalling In Irritable Bowel Syndrome. *Alimentary Pharmacology & Therapeutics* 23, 1067-76 (2006); Crowell, M. D. Role of Serotonin in the Pathophysiology of The Irritable Bowel Syndrome. *British Journal of Pharmacology* 141, 1285-93 (2004)), pulmonary (e.g. Lau, W. K. W. et al., The Role of Circulating Serotonin in the Development of Chronic Obstructive Pulmonary Disease. *PloS One* 7, e31617 (2012); Egermayer, P., Town, G. I. & Peacock, A. J. Role of Serotonin in the Pathogenesis of Acute and Chronic Pulmonary Hypertension. *Thorax* 54, 161-168 (1999)), inflammatory (e.g. Margolis, K. G. et al., Pharmacological Reduction of Mucosal but Not Neuronal Serotonin Opposes Inflammation in Mouse Intestine. *Gut* doi: 10.1 136/gutjnl-2013-304901 (2013); Duerschmied, D. et al., Platelet Serotonin Promotes the Recruitment of Neutrophils to Sites of Acute Inflammation in Mice. *Blood* 121, 1008-15 (2013); Li, N. et al., Serotonin Activates Dendritic Cell Function in the Context of Gut Inflammation. *The American Journal of Pathology* 178, 662-71 (2011)), or liver diseases or disorders (e.g. Ebrahimkhani, M. R. et al., Stimulating Healthy Tissue Regeneration by Targeting The 5-HT2B Receptor in Chronic Liver Disease. *Nature Medicine* 17, 1668-73 (2011)). The large number of pharmaceutical agents that block or stimulate the various 5-HT receptors is also indicative of the wide range of medical disorders that have been associated with 5-HT dysregulation (see for example: Wacker, D. et al., Structural Features for Functional Selectivity at Serotonin Receptors, *Science* (New York N.Y.) 340, 615-9 (2013)).

The rate-limiting step in 5-HT biosynthesis is the hydroxylation of tryptophan by dioxygen, which is catalyzed by tryptophan hydroxylase (TPH; EC 1.14.16.4) in the presence of the cofactor (6R)-L-erythro-5,6,7,8-tetrahydrobiopterin (BH4). The resulting oxidized product, 5-hydroxy tryptophan (5-HTT) is subsequently decarboxylated by an aromatic amino acid decarboxylase (AAAD; EC 4.1.1.28) to produce 5-HT. Together with phenylalanine hydroxylase (PheOH) and tyrosine hydroxylase (TH), TPH belongs to the pterin-dependent aromatic amino acid hydroxylase family.

Two vertebrate isoforms of TPH, namely TPH1 and TPH2, have been identified. TPH1 is primarily expressed in the pineal gland and non-neuronal tissues, such as entero chromaffin (EC) cells located in the gastrointestinal (GI) tract. TPH2 (the dominant form in the brain) is expressed exclusively in neuronal cells, such as dorsal raphe or myenteric plexus cells. The peripheral and central systems involved in 5-HT biosynthesis are isolated, with 5-HT being unable to cross the blood-brain barrier. Therefore, the peripheral pharmacological effects of 5-HT can be modulated by agents affecting TPH in the periphery, mainly TPH1 in the gut.

A small number of phenylalanine-derived TPH1 inhibitors are known. One example, p-chlorophenylalanine (pCPA), a very weak and unselective irreversible inhibitor of TPH, has proven effective in treating chemotherapy-induced emesis, as well as diarrhea, in carcinoid tumor patients. However, pCPA is distributed centrally and, as a result, its administration has been linked to the onset of depression and other alterations of CNS functions in patients and animals. p-Ethynyl phenylalanine is a more selective and more potent TPH inhibitor than pCPA (Stokes, A, H., et al. p-Ethynylphenylalanine: A Potent Inhibitor of Tryptophan Hydroxylase. *Journal of Neurochemistry* 74, 2067-73 (2000), but also affects central 5-HT production and, like pCPA, is believed to irreversibly interfere with the synthetic behavior of TPH (and possibly interact with other proteins).

More recently, bulkier phenylalanine-derived TPH inhibitors have been reported to reduce intestinal 5-HT concentration without affecting brain 5-HT levels (Zhong, H. et al., Molecular dynamics simulation of tryptophan hydroxylase-1: binding modes and free energy analysis to phenylalanine derivative inhibitors. *International Journal of Molecular Sciences* 14, 9947-62 (2013); Ouyang, L., et al., Combined Structure-Based Pharmacophore and 3D-QSA Studies on Phenylalanine Series Compounds as TPH1 Inhibitors. *International Journal of Molecular Sciences* 13, 5348-63 (2012); Camilleri, M. LX-1031, A Tryptophan 5-hydroxylase Inhibitor, and its Potential in Chronic Diarrhea Associated with Increased Serotonin. *Neurogastroenterology and Motility: The Official Journal of the European Gastrointestinal Motility Society* 23, 193-200 (2011); Cianchetta, G., et al., Mechanism of Inhibition of Novel Tryptophan Hydroxylase Inhibitors Revealed by Co-crystal Structures and Kinetic Analysis. *Current Chemical Genomics* 4, 19-26 (2010); Jin, H., et al., Substituted 3-(4-(1,3,5-triazin-2-yl)-phenyl)-2-aminopropanoic Acids as Novel Tryptophan Hydroxylase Inhibitors. *Bioorganic & Medicinal Chemistry Letters* 19, 5229-32 (2009); Shi, Z. C., et al., Modulation of Peripheral Serotonin Levels by Novel Tryptophan Hydroxylase Inhibitors for the Potential Treatment of Functional Gastrointestinal Disorders. *Journal of Medicinal Chemistry* 51, 3684-7 (2008); Liu, Q., et al., Discovery and Characterization of Novel Tryptophan Hydroxylase Inhibitors That Selectively Inhibit Serotonin Synthesis in the Gastrointestinal Tract. *The Journal of Pharmacology and Experimental Therapeutics* 325, 47-55 (2008)).

WO 2015/035113 discloses spirocyclic compounds that act as inhibitors of THP and are useful in the treatment of various diseases and disorders associated with peripheral serotonin, including cardiovascular diseases of pulmonary arterial hypertension (PAH) and associated pulmonary arterial hypertension (APAH) and carcinoid syndrome.

There is a need to selectively reduce tissue 5-HT (particularly intestinal 5-HT and lung 5-HT) levels as a means for treating and preventing 5-HT-associated diseases and modulation and/or reduction of serotonin levels, particularly peripheral serotonin levels. There is a particular need to treat or prevent bone disease, cardiovascular disease, metabolic disease, pulmonary disease, gastrointestinal disease, liver disease, cancer, and inflammatory disease. There is a more particular need to treat or prevent the cardiovascular diseases of pulmonary arterial hypertension (PAH) and associated pulmonary arterial hypertension (APAH). There is also a need to treat and prevent carcinoid syndrome. Thus, there is a need for a TPH1 inhibitor to address the foregoing diseases.

SUMMARY OF THE DISCLOSURE

The present disclosure provides a crystalline spirocyclic compound that is useful in the treatment of disease or disorders associated with peripheral serotonin.

The present disclosure also provides such a crystalline spirocyclic compound that is an inhibitor of tryptophan hydroxylase (TPH1), particularly the isoform 1 thereof, that is useful in the treatment of disease or disorders associated with peripheral serotonin.

The present disclosure further provides a crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate (hereinafter "Compound 1") that exhibits an XRPD pattern substantially as depicted in FIG. 1.

Further according to the present disclosure, there is provided a crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate that exhibits an XRPD pattern having a characteristic peak at 19.05±0.20 (° 2θ).

The present disclosure provides a pharmaceutical composition suitable for administration to a patient. The composition has the crystalline compound described above and one or more pharmaceutically acceptable excipients.

The present disclosure also provides a method of inhibiting TPH1. The method has the step of contacting the TPH1 with the crystalline compound described above.

Further according to the present disclosure, there is a method of lowering peripheral serotonin in a patient. The method has the step of administering to the patient the crystalline compound described above.

Still further according to the present disclosure, there is a method of treating or preventing a disease in a patient by lowering of peripheral serotonin. The method has the step of administering to the patient a therapeutically effective amount of the crystalline compound. The disease is selected from the group consisting of bone disease, cardiovascular disease, metabolic disease, pulmonary disease, gastrointestinal disease, liver disease, cancer, and inflammatory disease.

BRIEF DESCRIPTION OF THE DRAWINGS

Embodiments of the present disclosure are described herein with reference to the following figures.

DETAILED DESCRIPTION OF THE DISCLOSURE

Figure 1:
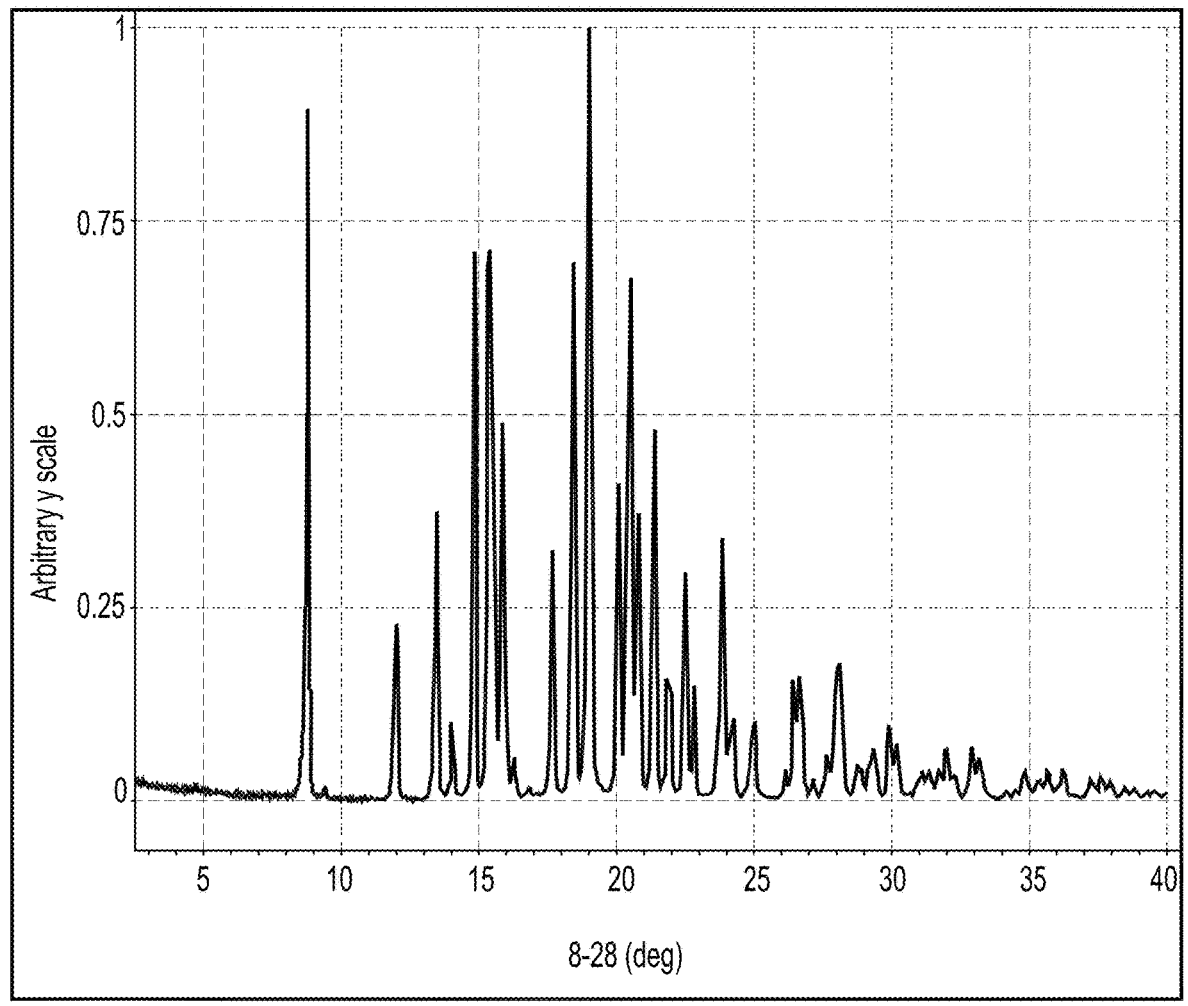
FIG. 1 is a plot of an XRPD of a crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate according to the present disclosure (crystalline Form 3).
Figure 2:
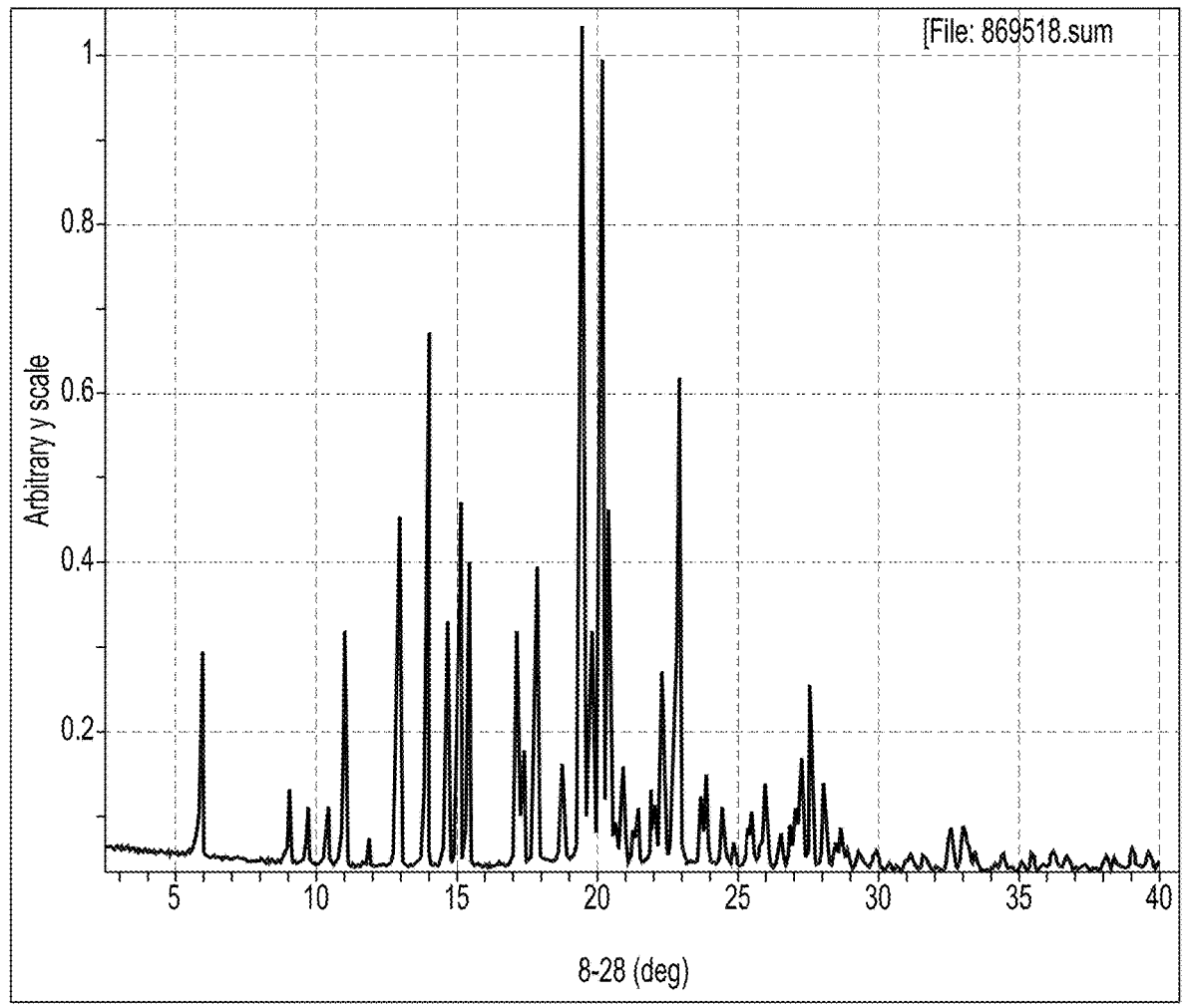
FIG. 2 is a plot of an XRPD of a crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate of a different polymorphic form than that of FIG. 1 (crystalline Form 1).

The crystalline Form 3 polymorph of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate of the present disclosure exhibits substantially greater thermodynamic stability supportive of longer shelf life compared to the crystalline Form 1 polymorph of the ethyl carboxylate compound, particularly at temperatures of less than 95° C. and more particularly at temperatures of less than 80° C.

The ethyl carboxylate compound has the following chemical structure:

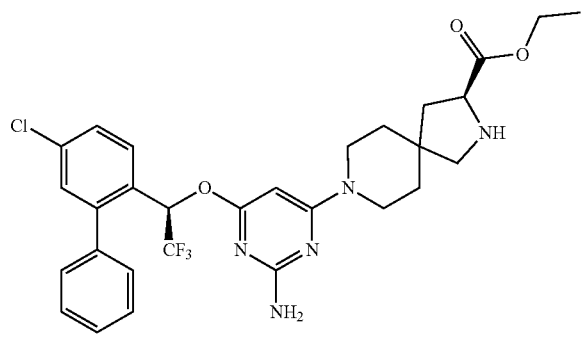 [SMILES: CCOC(=O)[C@@H]1CC2(CCN(c3cc(O[C@H](c4ccc(Cl)cc4-c4ccccc4)C(F)(F)F)nc(N)n3)CC2)CN1]

The Form 3 crystalline polymorph exhibits the XRPD (X-ray powder diffraction) pattern set forth below in Table 1.

TABLE 1

Observed Peaks for X-ray Powder Diffraction Pattern for Compound 1, Form 3

| Peak position (° 2θ) | d space (Å) | Intensity (%) |
|---|---|---|
| 8.78 ± 0.20 | 10.077 ± 0.235 | 90 |
| 12.00 ± 0.20 | 7.375 ± 0.125 | 25 |
| 13.47 ± 0.20 | 6.573 ± 0.099 | 39 |
| 14.02 ± 0.20 | 6.316 ± 0.091 | 12 |
| 14.87 ± 0.20 | 5.956 ± 0.081 | 71 |
| 15.39 ± 0.20 | 5.757 ± 0.075 | 72 |
| 15.61 ± 0.20 | 5.677 ± 0.073 | 78 |
| 15.89 ± 0.20 | 5.576 ± 0.071 | 50 |
| 16.31 ± 0.20 | 5.434 ± 0.067 | 7 |
| 17.70 ± 0.20 | 5.011 ± 0.057 | 34 |
| 18.45 ± 0.20 | 4.809 ± 0.052 | 70 |
| 19.05 ± 0.20 | 4.658 ± 0.049 | 100 |
| 20.12 ± 0.20 | 4.413 ± 0.044 | 42 |
| 20.57 ± 0.20 | 4.317 ± 0.042 | 68 |
| 20.84 ± 0.20 | 4.262 ± 0.041 | 39 |
| 21.46 ± 0.20 | 4.141 ± 0.039 | 49 |
| 21.94 ± 0.20 | 4.051 ± 0.037 | 18 |
| 22.56 ± 0.20 | 3.941 ± 0.035 | 31 |
| 22.90 ± 0.20 | 3.884 ± 0.034 | 17 |

TABLE 1-continued

Observed Peaks for X-ray Powder Diffraction Pattern for Compound 1, Form 3

| Peak position (° 2θ) | d space (Å) | Intensity (%) |
|---|---|---|
| 23.90 ± 0.20 | 3.723 ± 0.031 | 35 |
| 24.32 ± 0.20 | 3.660 ± 0.030 | 13 |
| 25.07 ± 0.20 | 3.552 ± 0.028 | 12 |
| 26.54 ± 0.20 | 3.359 ± 0.025 | 17 |
| 26.76 ± 0.20 | 3.332 ± 0.025 | 18 |
| 27.79 ± 0.20 | 3.210 ± 0.023 | 8 |
| 28.21 ± 0.20 | 3.163 ± 0.022 | 19 |
| 29.48 ± 0.20 | 3.030 ± 0.020 | 9 |

In another aspect, the Form 3 crystalline polymorph exhibits prominent XRPD peaks set forth below in Table 2.

TABLE 2

Prominent Observed Peaks for X-ray Powder Diffraction Pattern for Compound 1, Form 3

| Peak position (° 2θ) | d space (Å) | Intensity (%) |
|---|---|---|
| 8.78 ± 0.20 | 10.077 ± 0.235 | 90 |
| 14.87 ± 0.20 | 5.956 ± 0.081 | 71 |
| 15.39 ± 0.20 | 5.757 ± 0.075 | 72 |
| 15.61 ± 0.20 | 5.677 ± 0.073 | 78 |
| 18.45 ± 0.20 | 4.809 ± 0.052 | 70 |
| 19.05 ± 0.20 | 4.658 ± 0.049 | 100 |

In yet another aspect, the Form 3 crystalline polymorph exhibits a characteristic XRPD peak at 19.05±0.20 (° 2θ). The Form 3 crystalline polymorph is also variously referred to herein as "Form 3", "Compound 1, Form 3", "Form 3 compound" and "Form 3 crystalline compound".

The Form 1 crystalline compound exhibits the XRPD (X-ray powder diffraction) pattern set forth below in Table 3.

TABLE 3

Observed Peaks for X-Ray Powder Diffraction Pattern for Compound 1, Form 1

| Peak position (° 2θ) | d space (Å) | Intensity (%) |
|---|---|---|
| 5.92 ± 0.20 | 14.936 ± 0.522 | 27 |
| 9.01 ± 0.20 | 9.816 ± 0.222 | 11 |
| 9.68 ± 0.20 | 9.140 ± 0.192 | 9 |
| 10.38 ± 0.20 | 8.523 ± 0.167 | 9 |
| 10.95 ± 0.20 | 8.082 ± 0.150 | 30 |
| 11.85 ± 0.20 | 7.468 ± 0.128 | 6 |
| 12.90 ± 0.20 | 6.861 ± 0.108 | 43 |
| 13.89 ± 0.20 | 6.376 ± 0.093 | 65 |
| 14.62 ± 0.20 | 6.057 ± 0.084 | 31 |
| 15.04 ± 0.20 | 5.890 ± 0.079 | 44 |
| 15.41 ± 0.20 | 5.750 ± 0.075 | 38 |
| 17.13 ± 0.20 | 5.176 ± 0.061 | 30 |
| 17.83 ± 0.20 | 4.974 ± 0.056 | 37 |
| 18.72 ± 0.20 | 4.741 ± 0.051 | 14 |
| 19.44 ± 0.20 | 4.567 ± 0.047 | 100 |
| 19.79 ± 0.20 | 4.487 ± 0.045 | 30 |
| 20.11 ± 0.20 | 4.417 ± 0.044 | 97 |
| 20.34 ± 0.20 | 4.366 ± 0.043 | 44 |
| 20.84 ± 0.20 | 4.262 ± 0.041 | 14 |
| 21.41 ± 0.20 | 4.151 ± 0.039 | 10 |
| 21.88 ± 0.20 | 4.063 ± 0.037 | 11 |
| 22.28 ± 0.20 | 3.991 ± 0.036 | 25 |
| 22.83 ± 0.20 | 3.895 ± 0.034 | 60 |
| 23.85 ± 0.20 | 3.731 ± 0.031 | 13 |
| 24.40 ± 0.20 | 3.648 ± 0.030 | 9 |
| 25.45 ± 0.20 | 3.500 ± 0.027 | 9 |
| 25.97 ± 0.20 | 3.431 ± 0.026 | 12 |
| 27.22 ± 0.20 | 3.276 ± 0.024 | 15 |

TABLE 3-continued

Observed Peaks for X-Ray Powder Diffraction Pattern for Compound 1, Form 1

| Peak position (° 2θ) | d space (Å) | Intensity (%) |
|---|---|---|
| 27.58 ± 0.20 | 3.235 ± 0.023 | 23 |
| 28.06 ± 0.20 | 3.180 ± 0.022 | 12 |
| 28.66 ± 0.20 | 3.115 ± 0.021 | 7 |

In still another aspect, the Form 1 crystalline compound exhibits prominent XRPD peaks set forth below in Table 4.

TABLE 4

Prominent Observed Peaks for X-Ray Powder Diffraction Pattern for Compound 1, Form 1

| Peak position (° 2θ) | d space (Å) | Intensity (%) |
|---|---|---|
| 12.90 ± 0.20 | 6.861 ± 0.108 | 43 |
| 13.89 ± 0.20 | 6.376 ± 0.093 | 65 |
| 15.04 ± 0.20 | 5.890 ± 0.079 | 44 |
| 19.44 ± 0.20 | 4.567 ± 0.047 | 100 |
| 20.11 ± 0.20 | 4.417 ± 0.044 | 97 |
| 20.34 ± 0.20 | 4.366 ± 0.043 | 44 |
| 22.83 ± 0.20 | 3.895 ± 0.034 | 60 |

The amorphous form of the carboxylate compound can be prepared by the method set forth in Example 63i of U.S. Pat. No. 9,199,994, wherein Example 63i is specifically incorporated herein by reference. The amorphous form can then be converted to crystalline form by methods known in the art, including those described herein. The crystalline Forms 1 and 3 of the carboxylate compound can be prepared by the methods set forth in the examples below.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

Table 5 below sets forth some abbreviations used herein.

TABLE 5

| Abbreviations | |
|---|---|
| ACN | acetonitrile |
| APAH | associated pulmonary arterial hypertension |
| atm | atmosphere |
| CH$_3$CN | acetonitrile |
| CNS | central nervous system |
| ee | enantiomeric excess |
| EtOH | ethyl alcohol |
| h | hour(s) |
| IPC | In-process control |
| Ir catalyst | iridium catalyst |
| L | liter |
| μL | microliters |
| mbar | millibar |
| min | minute(s) |
| mg | milligram |
| mm | millimeter(s) |
| MeTHF | methyl tetrahydrofuran |
| MTBE | methyl t-butyl ether |
| N/A | not applicable |
| N.D. (ND) | not determined |
| PAH | pulmonary arterial hypertension |
| PheOH | phenylalanine hydroxylase |
| rel. vol. | Relative volume |
| RelWt/Vol | relative weight to volume |
| RT | room temperature |
| THF | tetrahydrofuran |
| TLC | thin-layer chromatography |
| TMSCI | trimethylsilyl chloride |
| TPH | tryptophan hydroxylase |
| V | relative volume |
| v/v | percent volume |
| wt % | weight percent |
| XRPD | x-ray powder diffraction |

Procedures for making the Form 3 compound are described herein below. Optimum reaction conditions and reaction times may vary depending on the particular reactants used. Unless otherwise specified, solvents, temperatures, pressures and other reaction conditions can be those known in the art. Specific procedures are provided in the Examples section below.

Typically, reaction progress may be monitored by thin layer chromatography (TLC) or HPLC-MS if desired. Intermediates and products may be purified by chromatography on silica gel, recrystallization, HPLC and/or reverse phase HPLC. In the reactions described below, it may be necessary to protect reactive functional groups (such as hydroxy, amino, thio, or carboxy groups) to avoid their unwanted participation in the reactions. The incorporation of such groups, and the methods required to introduce and remove them, are known to those skilled in the art (for example, see Greene, Wuts, *Protective Groups in Organic Synthesis, 2nd Ed.* (1999)). One or more deprotection steps in the synthetic schemes may be required to ultimately afford compounds of Formula I. The protecting groups depicted in the schemes are used as examples and may be replaced by other compatible alternative groups. Starting materials used in the following schemes can be purchased or prepared by methods described in the chemical literature, or by adaptations thereof, using methods known by those skilled in the art. The order in which the steps are performed can vary depending on the protecting or functional groups introduced and the reagents and reaction conditions used, but would be apparent to those skilled in the art.

The Form 3 compound can be used to inhibit the activity of the TPH1 enzyme in a cell by contacting the cell with an inhibiting amount of a compound of the disclosure. The cell can be part of the tissue of a living organism, or can be in culture, or isolated from a living organism. Additionally, the Form 3 compound can be used to inhibit the activity of the TPH1 enzyme in an animal, individual, or patient, by administering an inhibiting amount of a compound of the disclosure to the cell, animal, individual, or human patient.

The Form 3 compound can also lower peripheral serotonin levels in an animal, individual, or patient, by administering an effective amount of a compound of the disclosure to the animal, individual, or patient. In some embodiments, the Form 3 compound can lower levels of peripheral serotonin (e.g., 5-HT in the GI tract or lung tissue) selectively over non-peripheral serotonin (e.g., 5-HT in the CNS). In some embodiments, the selectivity can be 2-fold or more, 3-fold or more, 5-fold or more, 10-fold or more, 50-fold or more, or 100-fold or more.

As TPH1 inhibitors that can lower peripheral serotonin levels, the Form 3 compound is useful in the treatment and prevention of various diseases associated with abnormal expression or activity of the TPH1 enzyme, or diseases associated with elevated or abnormal peripheral serotonin levels. In some embodiments, the treatment or prevention includes administering to a patient in need thereof a therapeutically effective amount of a TPH1 inhibitor of the Form 3 compound. The Form 3 compound is also useful in the treatment and prevention of serotonin syndrome.

The efficacy of amorphous (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate in inhibiting TPH1 in mice was demonstrated in U.S. Pat. No. 9,199,994 in biological assays at Example 63i and Table 27. The entirety of U.S. Pat. No. 9,199,994 is incorporated herein by reference in its entirety.

Biological assays, some of which are described herein, can be used to determine the inhibitory effect of compounds against TPH (such as TPH1) in vitro and/or in vivo. In vitro biochemical assays for human, mouse, and rat TPH1 and human TPH2, PheOH, and TH may be used to measure inhibition of enzyme activity and the selectivity among TPH1, TPH2, PheOH, and TH. In addition, the efficacy of these compounds can be determined, for example, by measuring their effect on intestinal 5-HT levels in rodents after oral administration.

Diseases treatable or preventable by administering a TPH1 inhibitor of the disclosure include bone disease such as, for example, osteoporosis, osteoporosis pseudoglioma syndrome (OPPG), osteopenia, osteomalacia, renal osteodystrophy, Paget's disease, fractures, and bone metastasis, In some embodiments, the disease is osteoporosis, such as primary type 1 (e.g., postmenopausal osteoporosis), primary type 2 (e.g., senile osteoporosis), and secondary (e.g., steroid- or glucocorticoid-induced osteoporosis).

The present disclosure further includes methods of treating or preventing bone fracture such as, for example, osteoporotic or traumatic fracture, or surgical fractures associated with an orthopedic procedure (e.g., limb lengthening, bunion removal, an increase in bone formation associated with a prosthesis, bone metastasis, or spinal fusion).

Further diseases treatable or preventable by the methods of the disclosure include cardiovascular diseases such as atherosclerosis and pulmonary hypertension (PH), including idiopathic or familial PH, and including PH associated with or brought on by other diseases or conditions. In some embodiments, the PH disease is pulmonary arterial hypertension (PAH).

The types of PAH treatable according to the methods of the disclosure include (1) idiopathic (IPAH), (2) familial (FPAH), and (3) associated (APAH) which is the most common type of PAH. The latter is PAH which is associated with other medical conditions including, for example, (1) collagen vascular disease (or connective tissue disease) which include autoimmune diseases such as scleroderma or lupus; (2) congenital heart and lung disease; (3) portal hypertension (e.g., resulting from liver disease); (4) HIV infection; (5) drugs (e.g., appetite suppressants, cocaine, and amphetamines; and (6) other conditions including thyroid disorders, glycogen storage disease, Gaucher disease, hereditary hemorrhagic telangiectasia, hemoglobinopathies, myeloproliferative disorders, and splenectomy. APAH can also be PAH associated with abnormal narrowing in the pulmonary veins and/or capillaries such as in pulmonary veno-occlusive disease (PVOD) and pulmonary capillary hemangiomatosis. Another type of PAH is associated with persistent pulmonary hypertension of the newborn (PPHN).

Further diseases treatable or preventable by the methods of the present disclosure include metabolic diseases such as diabetes and hyperlipidemia; pulmonary diseases such as chronic obstructive pulmonary disease (COPD), and pulmonary embolism; gastrointestinal diseases such as IBD, colitis, chemotherapy-induced emesis, diarrhea, carcinoid syndrome, celiac disease, Crohn's disease, abdominal pain, dyspepsia, constipation, lactose intolerance, MEN types I and II, Ogilvie's syndrome, pancreatic cholera syndrome, pancreatic insufficiency, pheochromacytoma, scleroderma, somatization disorder, Zollinger-Ellison Syndrome, or other gastrointestinal inflammatory conditions; liver diseases such as chronic liver disease; cancers such as liver cancer, breast cancer, cholangiocarcinoma, colon cancer, colorectal cancer, neuroendocrine tumors, pancreatic cancer, prostate cancer, and bone cancer (e.g., osteosarcoma, chrondrosarcoma, Ewings sarcoma, osteoblastoma, osteoid osteoma, osteochondroma, enchondroma, chondromyxoid fibroma, aneurysmal bone cyst, unicameral bone cyst, giant cell tumor, and bone tumors); blood diseases (e.g., myeloproliferative syndrome, myelodysplasia syndrome, Hodgkin's lymphoma, non-Hodgkin's lymphoma, myeloma, and anemia such as aplastic anemia and anemia associated with kidney disease; and blood cancers (e.g., leukemias such as acute lymphocytic leukemia (ALL), chronic lymphocytic leukemia (CLL), acute myeloid leukemia (AML), and chronic myeloid leukemia (CML)).

The Form 3 compound is particularly useful in the treatment and prevention of carcinoid syndrome. Carcinoid syndrome is a paraneoplastic syndrome exhibiting the signs and symptoms that occur secondary to carcinoid tumors. Carcinoid syndrome is caused by a carcinoid tumor that secretes serotonin or other hormones into the bloodstream. Carcinoid tumors usually occur in the gastrointestinal tract, including the stomach, appendix, small intestine, colon, and rectum or in the lungs. Common symptoms include skin flushing, facial skin lesions, diarrhea, irritable bowel syndrome, cramping, difficulty breathing, and rapid heartbeat.

In some embodiments, the present disclosure includes methods of lowering plasma cholesterol, lowering plasma triglycerides, lowering plasma glycerol, lowering plasma free fatty acids in a patient by administering to said patient a therapeutically effective amount of a compound of the disclosure.

The Form 3 compound is also useful in the treatment and prevention of inflammatory disease, such as allergic airway inflammation (e.g., asthma).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the enzyme with a compound of the disclosure includes the administration of a compound of the present disclosure to an individual or patient, such as a human, having the TPH1 enzyme, as well as, for example, introducing a compound of the disclosure into a sample containing a cellular or purified preparation containing the TPH1 enzyme.

As used herein, the term "individual" or "patient" used interchangeably, refers to any animal, including mammals, preferably mice, rats, other rodents, rabbits, dogs, cats, swine, cattle, sheep, horses, or primates, and, most preferably, humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" refers to inhibiting onset or worsening of the disease; for example, in an individual who may be predisposed to the disease, condition or disorder but does not yet experience or display the pathology or symptomatology of the disease.

One or more additional pharmaceutical agents or treatment methods can be used in combination with the Form 3 compound for treatment or prevention of various diseases, disorders or conditions disclosed herein. The agents can be combined with Form 3 compound in a single dosage form, or the agents can be administered simultaneously or sequentially in separate dosage forms.

Examples of pharmaceutical agents that can be used in a combination therapy for blood disorders like blood cancers include parathyroid hormone, anti-sclerostin antibodies, cathepsin K inhibitors, and anti-Dickopff 1.

Examples of pharmaceutical agents that can be used in a combination therapy for cancer include leuprolide, goserelin, buserelin, flutamide, nilutamide, ketoconazole, aminoglutethimide, mitoxantrone, estramustine, doxorubicin, etoposide, vinblastine, paclitaxel, carboplatin, and vinorelbine. Therapies that can be combined with TPH inhibition include radiation therapy, high-intensity focused ultrasound, or surgery (e.g., removal of diseased tissues). Other drugs for use in treating cancer include testolactone, anastrozole, letrozole, exemestane, vorozole, formestane, fadrozole, GnRH-analogues, temozolomide, bavituximab, cyclophosphamide, fluorouracil, fulvestrant, gefitinib, trastuzumab, IGF-1 antibodies, lapatinib, methotrexate, olaparib, BSI-201, pazopanib, rapamycin, ribavirin, sorafenib, sunitinib, tamoxifen, docetaxel, vatalanib, bevacizumab, and octreotide.

Examples of pharmaceutical agents that can be used in combination therapy for cardiovascular or pulmonary diseases include endothelin receptor antagonists such as ambrisentan, BMS-193884, bosentan, darusentan, SB-234551, sitaxsentan, tezosentan and macitentan. Anticoagulants such as warfarin, acenocoumarol, phenprocoumon, phenindione, heparin, fondaparinux, argatroban, bivalirudin, lepirudin, and ximelagatran can also be useful in combination therapy. Pharmaceutical agents for combination therapy further include calcium channel blockers like amlodipine, felodipine, nicardipine, nifedipine, nimodipine, nisoldipine, nitrendipine, lacidipine, lercanidipine, phenylalkylamines, verapamil, gallopamil, diltiazem, and menthol. Prostacyclins like epoprostenol, iloprost and treprostinil can also be combined with the TPH inhibitors of the disclosure.

Further pharmaceutical agents for combination therapy in cardiovascular or pulmonary diseases include PDE5 inhibitors like sildenafil, tadalafil, and vardenafil; diuretics like furosemide, ethacrynic acid, torasemide, bumetanide, hydrochlorothiazide, spironolactone, mannitol, nitric oxide or nitric oxide releasers, and soluble guanylate cyclase stimulators, such as riociguat. Yet further pharmaceutical agents for combination therapy include APJ receptor agonists (WO 2013/11 11 10); IP receptor agonists (WO 2013/105057; WO 2013/105066; WO 2013/105061; WO 2013/105063; WO 2013/105065; WO 2013/105058); and PDGF receptor inhibitors (WO 2013/030802).

Examples of pharmaceutical agents that can be used in combination therapy for metabolic disorders include HSL inhibitors such as those disclosed in International Patent Publications WO2006/074957; WO2005/073199; WO2004/111031; WO2004/1 1 1004; WO2004/035550; WO2003/051841; WO2003/051842; and WO2001/066531.

Examples of pharmaceutical agents that can be used in combination therapy for bone disorders and diseases include bisphosphantes such as etidronate, clodronate, tiludronate, pamidronate, neridronate, oipadronate, alendronate, ibandronate, risedronate, cimadronate, zoledronate, and the like. Serotonin receptor modulators, such as 5-HTIB, 5-HT$_2$A, and 5-HT$_2$B agonists or antagonists, can also be useful in combination therapy for bone disease. Other useful agents for combination therapy include selective serotonin reuptake inhibitors (SS I), anti-serotonin antibodies, and beta blockers such as IPS339, ICI1 18,551, butaxamine, metipranolol, nadol, oxprenolol, penbutolol, pindolol, propranolol, timolol, and sotalol. Further useful agents for combination therapy for the treatment of bone disorders, such as osteoporosis, include teriparatide, strontium ranelate, raloxifene, and denosumab.

The Form 3 compound can be administered to patients (animals and humans) in need of such treatment in appropriate dosages that will provide prophylactic and/or therapeutic efficacy. The dose required for use in the treatment or prevention of any particular disease or disorder will typically vary from patient to patient depending on, for example, particular compound or composition selected, the route of administration, the nature of the condition being treated, the age and condition of the patient, concurrent medication or special diets then being followed by the patient, and other factors. The appropriate dosage can be determined by the treating physician.

The Form 3 compound can be administered orally, subcutaneously, topically, parenterally, by inhalation spray or rectally in dosage unit formulations containing pharmaceutically acceptable carriers, adjuvants and vehicles. Parenteral administration can involve subcutaneous injections, intravenous or intramuscular injections or infusion techniques. Treatment duration can be as long as deemed necessary by a treating physician. The compositions can be administered one to four or more times per day. A treatment period can terminate when a desired result, for example, a particular therapeutic effect, is achieved. Or a treatment period can be continued indefinitely.

In some embodiments, the pharmaceutical compositions can be prepared as solid dosage forms for oral administration (e.g., capsules, tablets, pills, dragees, powders, granules and the like). A tablet can be prepared by compression or molding. Compressed tablets can include one or more binders, lubricants, glidants, inert diluents, preservatives, disintegrants, or dispersing agents. Tablets and other solid dosage forms, such as capsules, pills and granules, can include coatings, such as enteric coatings.

Solid and liquid dosage forms can be formulated such that they conform to a desired release profile, e.g., immediate release, delayed release, and extended or sustained release.

The amount of spirocyclic compound to be administered will vary depending on factors such as the following: the spirocyclic compound selected, method of administration, release profile, and composition formulation. Typically, for the Form 3 spirocyclic compound in an oral dosage form to treat or prevent a disease, particularly PH/PAH/APAH/IPAH/FPAH, a typical dosage will be about 1 mg/kg/day to about 50 mg/kg/day and more typically from about 5 mg/kg/day to about 30 mg/kg/day, based on the weight of the patient. A most preferred spirocyclic compound is RVT-1201 in crystalline Form 3. Individual oral dosage forms typically have from about 50 mg to about 3000 mg of a spirocyclic compound and additional amounts of one or more pharmaceutically acceptable excipients. Other useful individual oral dosage forms can, by way of example, have spirocyclic compound in amounts of 100 mg, 150 mg, 200 mg, 250 mg, 300 mg, 350 mg, or 400 mg, 450 mg, 500 mg, 550 mg, 575 mg, 600 mg, 625 mg, 650 mg, 675 mg, 700 mg, 725 mg, 750 mg, 775 mg, 800 mg, 900 mg, 950 mg, 1000 mg, 1050 mg, 1100 mg, 1150 mg, and about 1200 mg, particularly 1200 mg. A preferred dosage is 1200 mg. Other amounts between 50 mg to 3000 mg are possible, for example, from about 325 mg to about 475 mg, from about 350 mg to about 500 mg, from about 375 to about 525 mg, from about 400 mg to about 550 mg, from about 425 mg to about 575 mg, from about 450 mg to about 600 mg, from about 475 mg to about 625 mg, from about 500 mg to about 650 mg, from about 525 mg to about 675 mg, from about 550 mg to about 700 mg, from about 575 mg to about 725 mg, from about 600 mg to about 750 mg, from about 625 mg to about 775 mg, from about 650 mg to about 800 mg, from about 675 mg to about 825 mg, from about 700 mg to about 850 mg, from about 725 mg to about 875 mg, from about 750 mg to about 900 mg, from about 775 mg to about 925 mg, from about 800 mg to about 950 mg, from about 825 to about 975, from about 850 mg to about 1000 mg, from about 900 mg to about 1150 mg, from about 1000 mg to about 1150 mg, from about 1100 mg to about 1250 mg, and from about 1200 mg to about 1350 mg.

"wt %" means weight percent based on the total weight of the composition or formulation.

Preferred dosage forms have the crystalline compound of Form 3 present in a proportion that is 90 wt % or more and more preferably 95 wt % or more by weight of any (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate present.

Dosage forms have the crystalline compound of Form 3 therein in any amount or proportion. Typical proportions include about 20 wt % or more, about 60 wt % or more, and about 90 wt % or more based on the total weight of the dosage form (with the balance predominantly excipients, carriers, and vehicles). Particularly useful proportions are 25 wt % and 60 wt %.

Compositions for inhalation or insufflation include solutions and suspensions in pharmaceutically acceptable aqueous or organic solvents, or mixtures thereof, and powders. Liquid dosage forms for oral administration can include, for example, pharmaceutically acceptable emulsions, microemulsions, solutions, suspensions, syrups and elixirs. Suspensions can include one or more suspending agents.

Dosage forms for transdermal administration of a subject composition include powders, sprays, ointments, pastes, creams, lotions, gels, solutions and patches.

The Form 3 compound and compositions containing same can be administered in the form of an aerosol, which can be administered, for example, by a sonic nebulizer.

Pharmaceutical compositions suitable for parenteral administration can include the Form 3 compound together with one or more pharmaceutically acceptable sterile isotonic aqueous or non-aqueous solutions, dispersions, suspensions or emulsions.

Alternatively, the composition can be in the form of a sterile powder which can be reconstituted into a sterile injectable solutions or dispersion just prior to use.

The following examples are illustrative of the disclosure and are not to be construed as limiting.

EXAMPLES

The Form 1 polymorph of Compound 1 of the present disclosure is prepared as described below.

Preparation of Compound 1

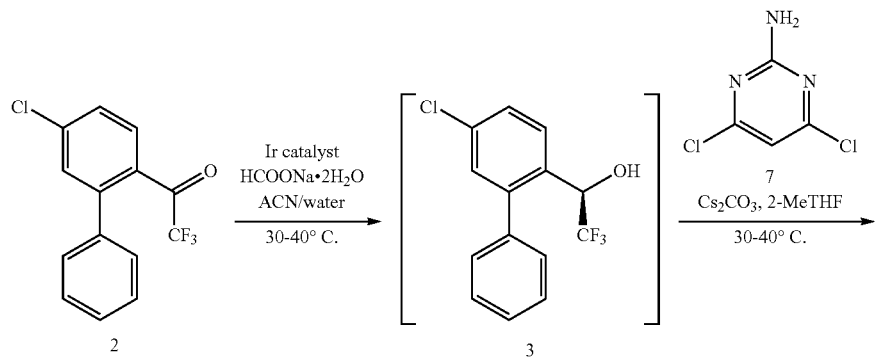

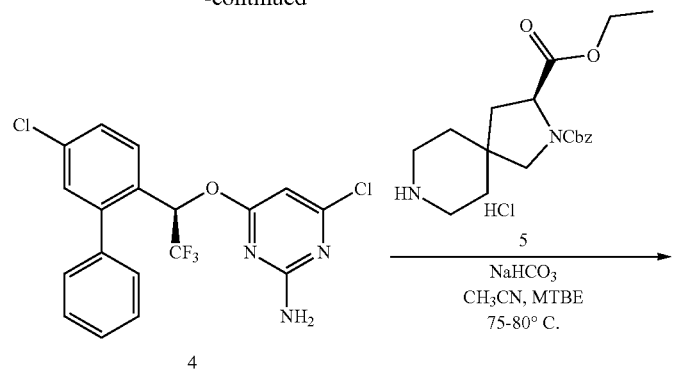
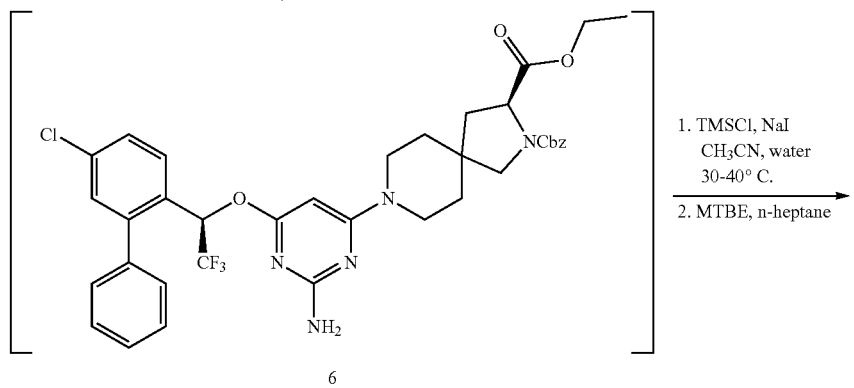
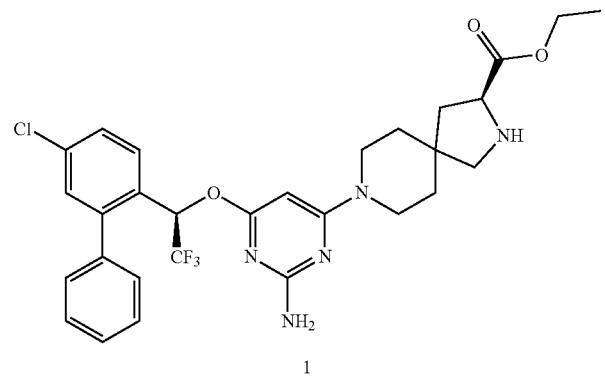
(R)-4-chloro-6-(1-(5-chloro-[1,1'-biphenyl]-2-yl)-2,2,2-trifluoroethoxy)pyrimidin-2-amine (Compound 4)
-continued
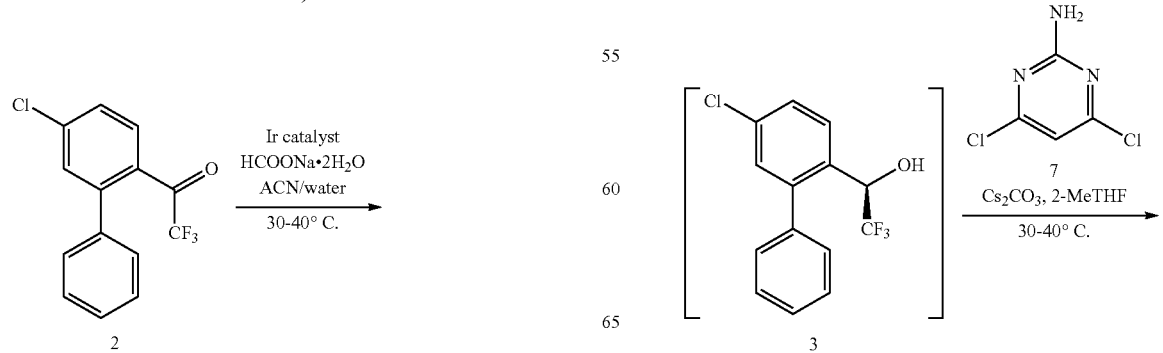

-continued

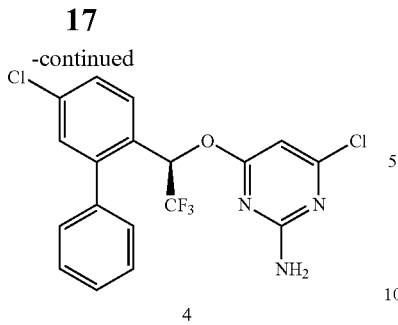

4

The ketone reduction was charged to the reactor under a N₂ atmosphere phenyl-2,2,2-trifluoroethanone (2) (2.54 kg) and acetonitrile (8 kg), followed by dichloro(pentamethylcyclopentadienyl)iridium (III) dimer (3.8 g) then an appropriate diamine ligand, such as N-((1S,2R)-2-amino-1,2-diphenylethyl)-4-methylbenzenesulfonamide (3.7 g). Process water (10.2 kg) and acetonitrile (1.4 kg) were then added. The mixture stirred for 2 to 6 hours while heated to 30-40° C., after which HCOONa.2H₂O (1.86 kg) was added slowly to the mixture. The mixture then stirred at 30-40° C. for 2 to 8 hours. The reaction was deemed to be complete when 1-(5-chloro-[1,1'-biphenyl]-2-yl)-2,2,2-trifluoroethan-1-one (2) had reached a level of 1%. The mixture was cooled to 20-30° C. then 2-MeTHF (13.0 kg) was added. The mixture was stirred for 30 minutes after which the aqueous phase was removed then the reaction solvent was switched to 2-MeTHF (190 wt % relative to 1-(5-chloro-[1,1'-biphenyl]-2-yl)-2,2,2-trifluoroethan-1-one (2)). Next, acetonitrile (20 kg) and Cs₂CO₃ (5.8 kg) were added at 20-30° C. under nitrogen protection, followed by slow addition of 4,6-dichloropyrimidin-2-amine (7) (1.5 kg). This mixture was heated to 55-65° C. where it stirred for 2 to 10 hours. The reaction was deemed complete when remaining 4,6-dichloropyrimidin-2-amine (7) was ≤1%. After cooling to 20-30° C., the mixture was passed through a pad of diatomite (2 kg) followed by a carbon cartridge. The reaction solvent was switched to methyl cyclohexane (840 wt % relative to 1-(5-chloro-[1,1'-biphenyl]-2-yl)-2,2,2-trifluoroethan-1-one (2)) at 35-40° C. The mixture was then cooled to 20-30° C. where it stirred for 10 to 16 hours, then further cooled to −25 to −15° C. where it stirred for 2 to 8 hours. Product (4) was collected by filtration onto filter cloth followed by drying under reduced pressure at 35-40° C. for 8 to 16 hours. The product thus obtained had an HPLC retention time matching the appropriate reference standard.

2-benzyl 3-ethyl (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-2,3-dicarboxylate (Compound 6)

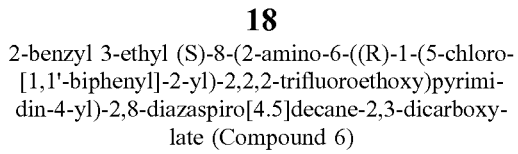

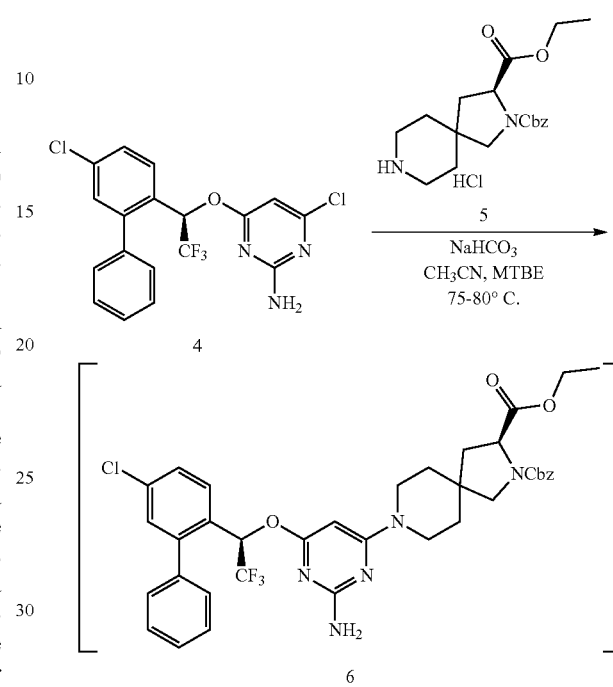

The reactor was charged with acetonitrile (11 kg), followed by compound 4 (2.4 kg), compound 5 (2.4 kg), and NaHCO₃ (1.5 kg). The reactor was inerted with N₂ then the contents were heated to 75-85° C. while stirring. The reaction was deemed complete when compound 4 reached 1.0% remaining. The mixture was cooled to 20-30° C. then MTBE (13 kg) was charged. This mixture was washed three times with a 5% aqueous H₂SO₄ solution (12 kg), discarding the aqueous phase after each wash. The organic solution was filtered through a bed of silica (2.3 kg) then rinsed the silica with MTBE (18.7 kg). The combined organics were solvent swapped to acetonitrile (13 kg) until the MTBE remaining was measured to be 0.05% w/w. The crude product was used as a solution in acetonitrile in the next step.

Preparation of Compound 1

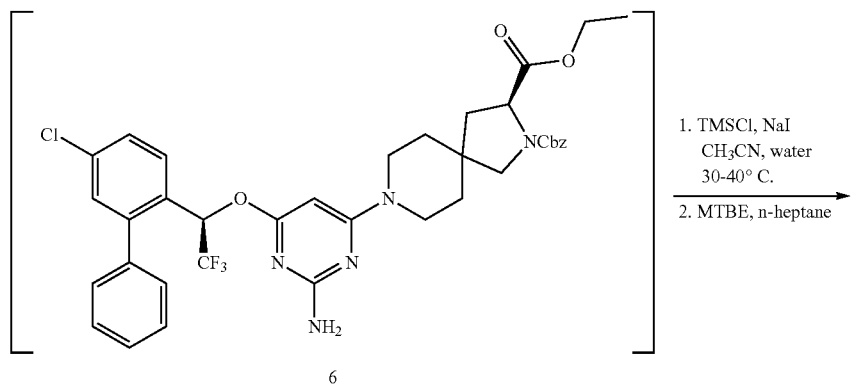

-continued

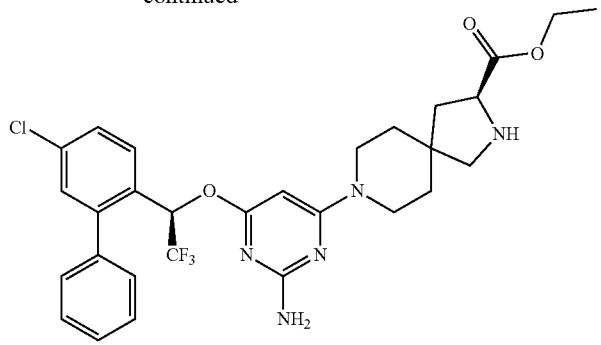

1

To the solution of compound 6 in acetonitrile was added NaI (3.5 kg) then the mixture was cooled to 10-20° C. TMSCI (2.5 kg) was added dropwise to the mixture while stirring at 10-20° C. for 1 to 2 hours. The mixture was then warmed to 30-40° C. where the mixture stirred for the next 22 to 24 hours. The reaction was deemed complete when compound 6 reached 1.0% remaining. Water was added after cooling to 10-20° C. This aqueous mixture was extracted with n-heptane (10.1 kg), then concentrated. The aqueous mixture was then extracted with MTBE (31 kg). The organic phase was then washed with aqueous $Na_2S_2O_3$ (1.7 kg in 11.7 kg of water) at 30-40° C. followed by 40% aqueous methylamine (1.5 kg). The organic phase was then washed with 8% aqueous methylamine (4.1 kg) followed by water (4.1 kg). The organic phase was dried then filtered through silica gel (3.7 kg). The filtrate was warmed to 40-50° C. n-Heptane (7.1 kg) was charged. After stirring for 1 hour, Compound 1 was added as seed material (52.4 g). After stirring for 2 hours at 40-50° C., n-heptane (69 kg) was added over 12 hours at 40-50° C. The mixture was cooled to 5-15° C. then filter the suspension. The solids were washed with 1:4 MTBE/n-heptane (28 kg) then n-heptane (7 kg). The solids were then dried under vacuum at 35-45° C. for 6 to 10 hours.

Recrystallization of Compound 1

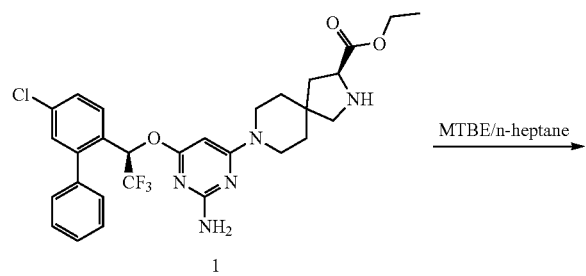

MTBE/n-heptane →

-continued

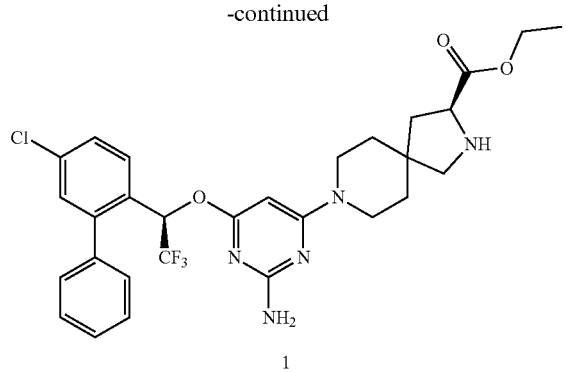

1

Crude Compound 1 (2.1 kg) was charged to a reactor followed by MTBE (5.4 kg). The mixture was heated to 40-50° C. then polish filtered. n-Heptane (5.6 kg) was added while stirring at 40-50° C. Next, Compound 1 (42.6 g) was charged as seed material. After stirring for 2 hours, n-heptane (17.1 kg) was charged over 10 hours. The mixture was cooled to 5-15° C. over 3.5 hours then stirred at this temperature for 7 hours. The mixture was filtered then the solids were washed with cold 1:4 MTBE/n-heptane (1.6 kg/5.7 kg) followed by cold n-heptane (1.4 kg). The wet solids were dried under vacuum at 35-45° C.

Solubility and Form Measurement

The solubility of Compound 1 was evaluated in organic solvents other than MTBE/n-heptane mixtures. The form of the residual solids was examined by XRPD. The results are as set forth in Table 6 below.

TABLE 6

| Solvent system | Ratio | T (° C.) | Solubility (mg/ml) | XRPD | Comments |
|---|---|---|---|---|---|
| IPA | N/A | 10 | 79.6 | Form1 | / |
|  |  | 50 | >518.1 | N/A | / |
| N-Butanol | N/A | 10 | 268.4 | Form1 | / |
|  |  | 50 | >757.9 | N/A | / |
| MTBE | N/A | 10 | >210.8 | N/A | / |
|  |  | 50 | >615.4 | N/A | / |
| n-Heptane | N/A | 10 | ~0 | Form1 | / |
|  |  | 50 | 9.5 | Form1 | / |
| Cyclohexane | N/A | 10 | N/A | mixture | / |
|  |  | 50 | N/A | Form1 | / |
| water | N/A | 10 | 0 | mixture | / |
|  |  | 50 | 1.2 | Form 1 | / |
| EtOH/ n-Heptane | 1:1 1:3 | 10 | 396.0 192.3 | Form 1 Form 1 | / |

TABLE 6-continued

| Solvent system | Ratio | T (° C.) | Solubility (mg/ml) | XRPD | Comments |
|---|---|---|---|---|---|
| Acetone/ | 1:1 | | >589.3 | N/A | Color changed |
| n-Heptane | 1:3 | | 208.0 | Form 1 | Color changed |
| EA/n- | 1:1 | | 422.1 | Form 1 | / |
| Heptane | 1:3 | | 115.1 | Form 1 | / |

Mixture = Form 1 + Form 3
IPA = isopropanol
EA = ethyl acetate
N/A = not applicable Competitive Slurry Compound 1 was also subjected to competitive slurry experiments between Compound 1, Form 1 and Compound 1, Form 3 in MTBE/n-heptane mixtures as summarized in Table 7 below.

TABLE 7

| Solvent system | Ratio | T (° C.) | XRPD (initial point) | XRPD (1~2 hours) | XRPD (19 hours) | XRPD (65 hours) |
|---|---|---|---|---|---|---|
| MTBE/n-heptane | 1/1(v/v) | 45 | Form 3 | Form 3 | Form 3 | ND |
| | 1/4(v/v) | | Form 1 + Form 3 | Form 1+ Form 3 | Form 3 | ND |
| | 1/5(v/v) | | Form 1 + Form 3 | Form + Form 3 | ND | Form 3 |
| | 1/4(v/v) | 10 | Form 1 + Form 3 | Form 1 + Form 3 | ND | Form 3 |
| | 1/5(v/v) | | Form 1 + Form 3 | Form 1 + Form 3 | ND | Form 3 |

Solubility of Compound 1, Form 3

The solubility of Compound 1 was evaluated in mixtures of MTBE/n-heptane mixtures at 10° C. and 45° C. The form of the residual solids was examined by XRPD. Results are set forth below in Table 8.

TABLE 8

Solubility and Form of Compound 1, Form 3 in Different Solvents

| Solvent | Starting Material | Solvent Ratio | T (° C.) | Solubility (mg/mL) | XRPD |
|---|---|---|---|---|---|
| MTBE/n-heptane | Compound 1, Form 3 | 1/1 | 45 | 89.4 | Form 3 |
| same | same | 1/0 | | >500 | N/A |
| same | same | 1/5 | | 4.2 | Form 3 |
| same | same | 1/4 | 10 | 6.2 | Form 3 |
| same | same | 1/2 | | 17.5 | Form 3 |
| same | same | 1/1 | | 27.2 | Form 3 |

Example 1

A Compound 1 material batch (CS14-075Aa-1702) was recrystallized in slurry in n-heptane with and without MTBE. The XRPD pattern of the material batch mainly conformed to Form 3 and contained two peaks of Form 1. The material batch was stirred for 4 hours in the solvent in different temperature conditions. The polymorphic form of the recrystallized Compound 1 was checked by XRPD. The results are set forth in Table 9.

TABLE 9

Recrystallization in n-Heptane and n-Heptane/MTBE

| Sample | Solvent | Temperature (° C.) | XRPD |
|---|---|---|---|
| ES928-S1-1 | n-heptane | 20 | Form 3 |
| ES928-S1-2 | n-heptane | 40 | Form 3 |
| ES928-S1-3 | n-heptane | 60 | Form 3 |
| ES928-S1-4 | MTBE/n-heptane | 20 | Form 3 |
| ES928-S1-5 | MTBE/n-heptane | 40 | Form 3 |
| ES928-S1-6 | MTBE/n-heptane | 60 | Form 3 |

All samples were verified by XRPD measurement as Form 3 (Compound 1). The different crystallization conditions did not affect the outcome.

One of the samples, ES928-S1-2, was checked by TGA/DSC as well. The TGA/DSC thermogram of sample ES928-S1-2 after 28 hours exhibited a melting event at T=107.2° C. and a gradual mass loss of 0.33% in temperature range 30° C.-240°. A batch of Compound 1, Form 1 material batch (lot FB1113-15) was measured for comparative purposes. The Form 1 material showed a melting event T peak=109.8° C. combined with a mass loss of 0.21% due to residual solvent. After the melting event, a mass loss of 0.95% was observed. The differences in thermal behavior can be related to the different forms that were measured by XRPD.

Example 2

A Compound 1 sample (ES928-52-1 of CS14-075Aa-1702) was recrystallized in solution with n-heptane and MTBE. The Compound 1 sample (50 mg, 1 eq.) was dissolved in MTBE (300 μL, 6 rel. vol.) at room temperature. n-Heptane (500 μL, 10 rel. vol.) was added stepwise until precipitation occurred. After adding 300 μL and 400 μL of n-heptane, the solution turned to a milky suspension. After adding another 100 μL, the mixture changed to almost clear solution with some sticky solid on the bottom of the vial. The mixture was left for one hour and a white suspension was obtained. XRPD measurement showed no changes in pattern to Form 1 but conversion to Form 3. At 28 hours, Form 3 was still obtained. TGA/DSC: Gradual mass loss of 0.97% and melting event at $T_{peak}$=105.0° C.

Example 3

A Compound 1 sample (ES928-52-2 of CS14-075Aa-1702) was recrystallized in solution with n-heptane and MTBE. The Compound 1 sample (50 mg, 1 eq.) was dissolved in MTBE (100 μL, 2 rel. vol.) at room temperature. n-Heptane (100 μL, 2 rel. vol.) was added to the mixture and cooled to room temperature. The mixture was left for one hour and a white suspension was obtained. XRPD measurement showed no changes in pattern to Form 1 but conversion to Form 3. At 5 hours and 21 hours, Form 3 was still obtained. TGA/DSC: Gradual mass loss of 0.15% and melting event at $T_{peak}$=107.1° C.

Example 4

Compound 1 samples ES928-53-1, ES928-53-2, and ES928-53-3 of CS14-075Aa-1702 were recrystallized in solution with n-heptane and MTBE. The Compound 1 samples (24.95 mg, 1 eq.) were each dissolved in MTBE (175 μL, 7 rel. vol.) at 25° C. n-Heptane (37.5 ml, 1.5 rel. vol.) was added to the solutions. Temperature remained at 25.2° C. The mixture was left in vacuum conditions (250 mbar) to distill MTBE (55 mL, 48.78 g). Again n-heptane (25 mL, 1 rel. vol.) was added to the mixture and the distillation procedure was repeated. The mixture was left for 1 hour. Took IPC 1: ES928-53-1. The mixture was cooled to 10° C. Again, the mixture was left for 16 hours. Took IPC 2: ES928-53-2. Temperature was raised to 25° C. to dissolve the product again in MTBE (7 rel. vol.). n-Heptane (7 rel. vol.) and distillated MTBE were dosed volume was kept constant by adding n-heptane. A few seeds of Form 1 (14-075Aa-1601 recrystallized) were added but they dissolved. After distillation of 124.6 g MTBE, new seeds of Form 1 were added, which resulted in a hazy mixture. Distillation was continued. After one hour, a white slurry was obtained. Took IPC-3: ES928-53-3. Distillation was discontinued after 57.85 g of solvent was obtained. The product was filtrated and dried at ambient conditions. Samples were checked by TGA/DSC and stored in vacuum conditions. During second distillation, precipitation occurred. (volume distillate—65 mL). XRPD yielded Form 3 for each of IPC 1: ES928-53-1, IPC 2: ES928-53-2, and IPC 3: ES928-53-3->Form 3.

Example 5

Competitive slurry experiments were performed to ascertain if Compound 1 samples of Form 1 and mixtures of Form 1 and Form 3 can be converted to Form 3. Pure Form 1 and Form 3 were also tested. First, 700 mg of Compound 1 were added in different ratios to 10 volumes of n-heptane and stirred for three days (Table 2). After 16 hours and four days, the samples were checked for polymorphic form by XRPD. All experiments showed complete conversion to Form 3. After 16 hours, the experiment starting with Form 1 remained as Form 1 but slowly converts to Form 3 over 4 days. Results are in Table 10 below.

TABLE 10

Competitive Slurry Experiments of Example 7

| Samples | Form 1 (%) | Form 3 (%) | Mixture of Form 1 and Form3 (%) | XRPD 16 hours | XRPD 4 days |
|---|---|---|---|---|---|
| ES928-60-1 | 100 | 0 | n.a. | Form 1 | Form 3 |
| ES928-60-2 | 99 | 1 | n.a. | Mixture 1 and 3 | Form 3 |
| ES928-60-3 | 50 | 50 | n.a. | Form 3 | Form 3 |
| ES928-60-4 | 1 | 99 | n.a. | Form 3 | Form 3 |
| ES928-60-S | 0 | 100 | n.a. | Form 3 | Form 3 |
| ES928-60-6 | 33 | 33 | 33 | Form 3 | Form 3 |

Example 6

Additional tests were performed to understand the differences between form 1 and 3. One of those tests was to check stability of polymorph form by pH measurement at several times when the different forms were stirred in water (Table 11). During the tests, any changes in polymorph form were checked. XRPD measurement did not show any change in polymorphic form after slurry in water.

TABLE 11

Stability Test of Form 1, Form 3, and a Mixture of Forms 1 and 3.

| Samples | pH (2 hours) | pH (4 hours) | pH (7 hours) |
|---|---|---|---|
| ES928-59-1 (mixture 1, 3) | 8.68 | 8.22 | 8.05 |
| ES928-59-2 (form 1) | 8.26 | 7.75 | 7.76 |
| ES928-59-3 (form 3) | 8.71 | 8.65 | 8.32 |

Example 7

Solubility determination of Forms 1 and 3 showed small differences (Table 12). The method applied was a shake-flask solubility determination with stepwise addition of the solvent until complete dissolution is observed visually. This results in solubility ranges.

TABLE 12

Solubility Determination of Form 1 and Form 3 by Shake-Flask(mg/mL)

| Solvent | Solubility Form 1 | Solubility Form 3 |
|---|---|---|
| methanol | 99-990 | 102-1020 |
| methyl tert-butyl ether | 102-1020 | 106-1060 |
| acetone | 96-960 | 108-1080 |
| tetrahydrofuran | 97-970 | 99-990 |
| ethyl acetate | 101-1010 | 95-950 |
| ethanol | 96-960 | 33-100 |
| 2-methyl-tetrahydrofuran | 97-970 | 106-1060 |
| 2-propanol | 98-980 | <10.1 |
| acetonitrile | 99-990 | 99-990 |
| isopropyl acetate | 103-1030 | 94-940 |
| l-propanol | 101-1010 | 35-104 |
| n-heptane | <10.1 | <9.9 |
| toluene | 98-980 | 105-1050 |
| water | <10.0 | <10.0 |
| formic acid 99% | 97-970 | 96-960 |
| acetic acid | 32-95 | 104-1040 |
| methyl isobutyl | 99-990 | 100-1000 |
| N,N-dimethyl-acetamide | 96-960 | 108-1080 |
| dimethyl sulfoxide | 101-1010 | 109-1090 |

Because of the small differences in solubilities, HPLC was used to measure the solubilities. The values were conformed to the shake-flask results. In time, the remaining slurry of Form 3 in ethanol dissolved completely. In alcohol, there was a difference in dissolution rate. This difference was not observed for aqueous solutions.

TABLE 13

Solubility Determination of Form 1 and Form 3 by HPLC

| Sample | Form | Solvent | Area | Conc. Actual mg/mL |
|---|---|---|---|---|
| ES-928-62-1 | 1 | Buffer pH 1.2 | 1581022 | 49 |
| ES-928-62-4 | 3 | Buffer pH 1.2 | 1493705 | 46 |
| EdA-928-63-1 | 1 | Ethanol Abs. | 3975890 | 129 |
| EdA-928-63-2 | 3 | Ethanol Abs. | 1851577 | 58 |

It should be understood that the foregoing description is only illustrative of the present disclosure. Various alternatives and modifications can be devised by those skilled in the art without departing from the present disclosure. Accordingly, the present disclosure is intended to embrace all such alternatives, modifications and variances which fall within the scope of the appended claims.

What is claimed is:

1. A crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate that exhibits an XRPD pattern substantially as depicted in FIG. 1.

2. A pharmaceutical composition suitable for administration to a patient, comprising: the crystalline compound of claim 1 and one or more pharmaceutically acceptable excipients.

3. A method of lowering peripheral serotonin in a patient in need thereof, comprising administering to the patient an effective amount of the crystalline compound of claim 1.

4. A method of treating or preventing pulmonary arterial hypertension (PAH) in a patient in need thereof, the method comprising administering to said patient in need thereof a therapeutically effective amount of the crystalline compound of claim 1.

5. The method of claim 4, wherein the PAH is associated pulmonary arterial hypertension (APAH).

6. A dosage form suitable for administration to a patient, the dosage form comprising: the crystalline compound of claim 1 is present in a proportion that is 90 wt % or more by weight of any (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate present.

7. The dosage form of claim 6, wherein the crystalline compound is present in a proportion that is 95 wt % or more by weight of any (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate present.

8. A dosage form suitable for administration to a patient, the dosage form comprising: the crystalline compound of claim 1 in a proportion that is about 20 wt % or more by weight of the dosage form.

9. The dosage form of claim 6, wherein the dosage form has an immediate release profile.

10. The dosage form of claim 6, wherein the dosage form is an inhalant.

11. A method of crystallizing or recrystallizing (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate, comprising:
   (A) contacting the (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate with an amount of heptane sufficient to form a suspension thereof; and
   (B) removing the heptane from the suspension or filtrating the suspension to form crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate.

12. A method of crystallizing or recrystallizing (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate, comprising:
   (A) dissolving the (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate in an amount of methyl tert-butyl ether following by introducing an amount of heptane sufficient to form a suspension thereof; and
   (B) removing the heptane from the suspension or filtrating the suspension to form crystalline (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate.

* * * * *